(12) United States Patent
Bock et al.

(10) Patent No.: US 8,211,956 B2
(45) Date of Patent: Jul. 3, 2012

(54) UNIVERSAL DENTAL ADHESION-PROMOTER COMPOSITION

(75) Inventors: Thorsten Bock, Tosters (AT); Norbert Moszner, Triesen (LI); Volker M. Rheinberger, Vaduz (LI); Ulrich Salz, Lindau (DE); Frank Zeuner, Schellenberg (LI)

(73) Assignee: Ivoclar Vivadent AG, Schaan (LI)

( * ) Notice: Subject to any disclaimer, the term of this patent is extended or adjusted under 35 U.S.C. 154(b) by 124 days.

(21) Appl. No.: 12/491,815

(22) Filed: Jun. 25, 2009

(65) Prior Publication Data

US 2010/0240796 A1 Sep. 23, 2010

(30) Foreign Application Priority Data

Mar. 17, 2009  (EP) .................................. 09155324

(51) Int. Cl.
*A61K 6/00* (2006.01)
(52) U.S. Cl. ...................................................... 523/118
(58) Field of Classification Search .................... 523/118
See application file for complete search history.

(56) References Cited

U.S. PATENT DOCUMENTS

| | | | |
|---|---|---|---|
| 4,612,384 A | 9/1986 | Omura et al. | |
| 5,085,726 A * | 2/1992 | Omura et al. | 156/307.3 |
| 5,670,657 A * | 9/1997 | Kojima et al. | 549/39 |
| 2002/0198284 A1 * | 12/2002 | Nakatsuka et al. | 523/116 |
| 2006/0135719 A1 | 6/2006 | Moszner et al. | |
| 2009/0076182 A1 | 3/2009 | Tanaka et al. | |

FOREIGN PATENT DOCUMENTS

| | | |
|---|---|---|
| DE | 10 2005 002 750 A1 | 7/2006 |
| EP | 0 224 319 A1 | 6/1987 |
| EP | 1 911 434 A | 4/2008 |
| JP | 63051308 A | 3/1988 |
| JP | 7277913 A | 10/1995 |
| WO | 2008/053990 A1 | 5/2008 |

OTHER PUBLICATIONS

Kern et al., "Eine einfache Versuchsanordnung zur universellen Prufung des Klebeverbundes im axialen Zugtest," Dtsch Zahnarztl Z 48:769-772 (1993).
Kern et al., "Bonding to Glass Infiltrated Alumina Ceramic: Adhesive Methods and Their Durability," J. Prosthet. Dent. 73:240-249 (1995).
Kern et al., "Bonding to Zirconia Ceramic: Adhesion Methods and Their Durability," Dent. Mater. 14:64-71 (1998).
Mathias et al., "New Difunctional Methacrylate Ethers and Acetals: Readily Available Derivatives of Alpha-Hydroxymethyl Acrylates," Macromolecules 20:2039-2041 (1987).
Yoshida et al., "Shear Bond Strength of a New Resin Bonding System to Different Ceramic Restorations," Int. J. Prosthodont. 20:417-418 (2007).
European Search Report for priority application No. EP09155324.8, Aug. 6, 2009.

* cited by examiner

*Primary Examiner* — Mark Eashoo
*Assistant Examiner* — David Karst
(74) *Attorney, Agent, or Firm* — Ann M. Knab; Thad McMurray

(57) ABSTRACT

The invention relates to an adhesion-promoter composition for the adhesive joining of metallic or ceramic dental materials to radically curing dental materials, wherein the adhesion-promoter composition contains an alkoxysilane monomer (i), a phosphoric acid ester monomer (ii), a sulphur-containing monomer (iii) and an organic solvent (iv).

6 Claims, No Drawings

UNIVERSAL DENTAL ADHESION-PROMOTER COMPOSITION

This application claims the benefit of European Patent Application Serial No. 09155324.8, filed Mar. 17, 2009, which is hereby incorporated by reference in its entirety.

FIELD

The present invention relates to a dental adhesion-promoter composition for the adhesive joining of different metallic or ceramic dental materials to radically curing dental materials, preferably composites.

BACKGROUND

It is often necessary in tooth restoration to combine radically curing dental materials, in particular formulations which contain inorganic fillers in a radically curable organic matrix (so-called composites), with other metal- or mineral-based dental restoration materials. In particular, in the case of restoration materials, a distinction is drawn between the following material types: noble metals (e.g. gold, platinum, palladium, silver and their alloys), base metals (e.g. chromium, nickel, molybdenum, titanium and their alloys), siliceous ceramics (e.g. feldspar, quartz, leucite-based ceramics or glass ceramic) or non-siliceous ceramics (e.g. yttrium-stabilized zirconium oxide, aluminium oxide, glass-infiltrated aluminium oxide). Adhesion promoters (primers) are used to improve the adhesion between the aforementioned restoration materials and the radically curing dental material. Primers known to date for adhesively securing dental restoration materials are normally suitable in each case for only one of the named material types and do not offer clinically useful adhesion to other substrates.

DE 10 2005 002 750 A1 discloses a primer for dental noble metal alloys that contains special disulphides substituted with polymerizable groups.

EP 0 224 319 A1 describes a primer composition for improving adhesion to various ceramic materials that contains a silane which can be hydrolyzed to an organofunctional silanol. Although an improvement in adhesion to metal materials is also demonstrated in EP 0 224 319 A1, it transpires in practice that the described primers act only on siliceous ceramics.

The subject of JP 2601254 B2 is a dental primer for ceramics and metal which contains the combination of an organo-functional silane with special (meth)acryloyloxy-functional phosphoric acid monoesters. JP 2593850 B2 describes a dental adhesive composition which contains inter alia an organo-functional silane and an acid organic phosphorus compound with a radically polymerizable double bond. The composition is said to make possible bonding to both metals and ceramics. However, on noble metal surfaces, such as gold, no chemical bonding is effected with the two compositions named above and thus there can be no durable bond between metal and a radically curing dental material with these compositions, in particular because of the different coefficients of thermal expansion of the materials to be joined.

WO 2008/053990 also discloses a dental adhesive composition which contains the combination of a silane coupling agent with special (meth)acryloyloxy-functional phosphoric acid monoesters. The composition is said to display a good adhesion both to dental ceramics and to organic composites which contain inorganic materials.

The scientific literature reports that specific adhesion monomers are especially suitable for special types of metal or ceramic (see for example Kern M, Wegner M S, "Bonding to Zirconia Ceramic: Adhesion Methods and Their Durability", Dent Mater 1998, 14; 64-71; Yoshida K, Kamada K, Atsuta M, "Shear Bond Strength of a New Resin Bonding System to Different Ceramic Restorations", Int. J. Prosthodont 2007, 20; 417-418).

However, a disadvantage of using substrate-specific primer systems is that because of the variety of substrate types a corresponding number of primers becomes necessary. However, in the case of clinical use, as the number of substrate-specific primer systems increases, so does the danger of confusion and thus also the risk of clinical failure. In addition, a precise application of a substrate-specific primer is clinically not possible in many cases, such as for example when repairing a fractured ceramic veneer, since there is more than one substrate directly next to each other in a narrow space.

Accordingly the object of the invention is to provide a universal adhesion promoter that is characterized by a good bonding effect between a radically curing dental material, in particular a composite, and many other dental restoration materials. A good bonding effect is also to be preserved after an alternating thermal load.

DETAILED DESCRIPTION

The object is achieved by an adhesion-promoter composition, containing
(i) at least one alkoxysilane monomer of the general formula $$R^1_n Si(OR^2)_{4-n} \quad (I),$$

in which
$R^1$ represents a residue which has at least one polymerizable group,
$R^2$ represents a $C_1$ to $C_8$ alkyl residue, preferably $C_1$ to $C_4$ alkyl residue and
n is 1, 2 or 3,
wherein the residues $R^1$ and $R^2$ can each be the same or different;
(ii) at least one phosphoric acid ester monomer of the general formula $$O=P(OR^3)_m(OR^4)_{3-m} \quad (II),$$

in which
$R^3$ represents a residue which has at least one polymerizable group,
$R^4$ represents a residue selected from H, silyl, preferably $SiMe_3$, and $C_1$ to $C_{16}$ alkyl, in particular $C_1$ to $C_4$ alkyl, and
m is 1 or 2,
wherein the residues $R^3$ and $R^4$ can each be the same or different;
(iii) at least one sulphur-containing monomer of the general formula $$R^5\!-\!R^6\!-\!S_x\!-\!R^6\!-\!R^5 \quad (IIIa)$$

or $$R^5\!-\!R^6\!-\!S_x\!-\!R^7 \quad (IIIb),$$

in which
x is an integer from 1 to 8, preferably 2,
$R^5$ represents a residue which has at least one polymerizable group and the two $R^5$ in formula (IIIa) can be the same or different,
$R^6$ represents an unsubstituted or substituted $C_1$ to $C_{30}$ alkylene residue and the two $R^6$ in formula (IIIa) can be the same or different,
$R^7$ represents H or an unsubstituted or substituted $C_1$ to $C_{26}$ alkyl residue,
wherein the two residues $R^6$ in formula (IIIa) or $R^6$ and $R^7$ in formula (IIIb) can be joined to each other to form a heterocycle with $S_x$, and (iv) organic solvent.

Suitable substituents of the above alkylene or alkyl residues ($R^6$, $R^7$) are aryl, alkylaryl, heteroalkyl, heteroaryl, heteroalkylaryl, urethane, halogen, isocyanate, ureido, and/or imidazolinyl groups as well as aryl, alkylaryl, heteroalkyl, heteroaryl, and/or heteroalkylaryl residues which are substituted with urethane, halogen, isocyanate, ureido, imidazolinyl groups, acryloyloxy and/or methacryloyloxy groups, in particular with urethane, halogen, isocyanate, ureido, and/or imidazolinyl groups.

The invention also relates to the use of the adhesion-promoter composition in dentistry and dental engineering, in particular the use for the adhesive joining of metallic or ceramic dental materials to radically curing dental materials, preferably composites and composites-based fixing materials (cements).

Component (i), the at least one alkoxysilane monomer of formula $R^1{}_n Si(OR^2)_{4-n}$ (I), has, in addition to the hydrolyzable alkoxy group —$OR^2$, at least one residue $R^1$ which contains at least one, preferably exactly one, polymerizable group. It is typically a radically polymerizable group. Preferably, the alkoxysilane has one or two $R^1$ residues. The $R^1$ residue preferably cannot be hydrolyzed. $R^1$ preferably contains an ethylenically unsaturated double bond. For example $R^1$ can contain a (meth)acryloyloxy group ($H_2C$=$C(R^8)$—CO—O— with $R^8$=$CH_3$ or H), a (meth)acryloylamino group ($H_2C$=$C(R^9)$—CO—NH— with $R^9$=$CH_3$ or H), a vinyl, allyl or styryl group, wherein the groups can be unsubstituted or substituted by suitable substituents. Preferred residues $R^1$ include (meth)acrylbyloxyalkyl, preferably (meth)acryloyloxy $C_2$-$C_{16}$ alkyl, particularly preferably (meth)acryloyloxypropyl; (meth)acryloylaminoalkyl, preferably (meth)acryloylamino $C_2$-$C_{16}$ alkyl, particularly preferably (meth)acryloylaminopropyl; vinyl; allyl and styryl.

The alkyl residue $R^2$ of the alkoxy group in formula (I) has 1 to 8 C atoms and is preferably straight-chained or branched. $R^2$ is preferably a methyl, ethyl, n- or i-$C_3$-$C_8$ residue, particularly preferably methyl or ethyl.

Particularly suitable alkoxysilane monomers (i) for the present invention are:

3-methacryloyloxypropyltrimethoxysilane (=3-trimethoxysilyl propyl methacrylate) (MPTMS)

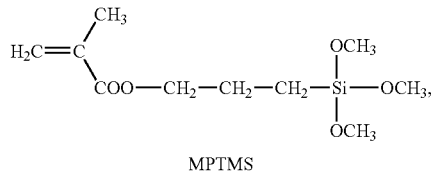

MPTMS 3-methacryloyloxypropyltriethoxysilane (=3-triethoxysilyl propyl methacrylate) (MPTES)

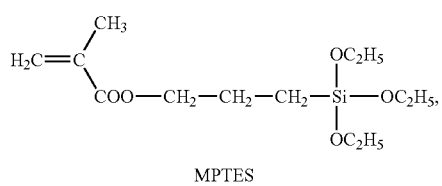

MPTES

Di(3-methacryloyloxypropyl)dimethoxysilane (DPDMS)

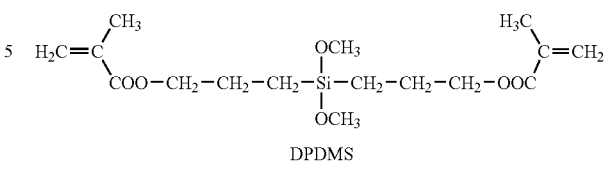

DPDMS and methacrylic acid (3-trimethoxysilylpropyl) amide (MTPA)

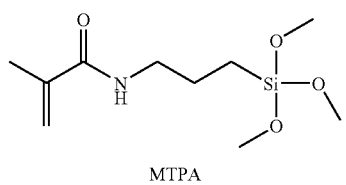

MTPA

The most preferred alkoxysilane monomer is 3-methacryloyloxypropyltrimethoxysilane.

Component (i) is typically present in the adhesion-promoter composition according to the invention in a quantity of 0.05 to 25.0% by weight, preferably 0.2 to 10.0% by weight and particularly preferably 0.5 to 5.0% by weight, in each case based on the total weight of the composition.

Component (ii), the at least one phosphoric acid ester monomer of the general formula O=$P(OR^3)_m(OR^4)_{3-m}$ (II), has at least one residue $R^3$ which contains at least one, preferably one or two, polymerizable groups. It is typically (a) radically polymerizable group(s). The phosphoric acid ester preferably has exactly one $R^3$ residue and thus has the following formula (IIa).

Formula (IIa)

$R^3$ in formula (II) or (IIa) preferably contains at least one ethylenically unsaturated double bond. For example $R^3$ can contain at least one (meth)acryloyloxy group, a (meth)acryloylamino group, a vinyl, allyl or styryl group or a combination thereof, wherein the groups can be unsubstituted or substituted by suitable substituents. Preferred residues $R^3$ include (meth)acryloyloxyalkyl, preferably (meth)acryloyloxy $C_2$-$C_{16}$ alkyl, particularly preferably (meth)acryloyloxy $C_4$-$C_{14}$ alkyl, very particularly preferably (meth)acryloyloxy $C_6$-$C_{10}$ alkyl; di(meth)acryloyloxyalkyl, preferably di(meth)acryloyloxy $C_2$-$C_{16}$ alkyl, particularly preferably di(meth)acryloyloxy $C_2$-$C_{10}$ alkyl, particularly preferably di(meth)acryloyloxyisopropyl; (meth)acryloylaminoalkyl, preferably (meth)acryloylamino $C_2$-$C_{16}$alkyl, particularly preferably (meth)acryloylamino $C_4$-$C_{14}$ alkyl very particularly preferably (meth)acryloylamino $C_6$-$C_{10}$ alkyl; vinyl; allyl and styryl.

The $R^4$ residue is selected from H, silyl, preferably $SiMe_3$, and $C_1$ to $C_{16}$ alkyl, wherein the alkyl residue is preferably straight-chained or branched, particularly preferably methyl, ethyl or an n- or i-$C_3$-$C_{16}$ residue. In a particularly preferred embodiment $R^4$ is H, wherein the dihydrogen phosphates (phosphoric acid monoesters) represent the most preferred phosphoric acid ester monomers.

Particularly suitable phosphoric acid ester monomers (ii) for the present invention are:

1-methacryloyloxydecane-10-phosphate (MDP)

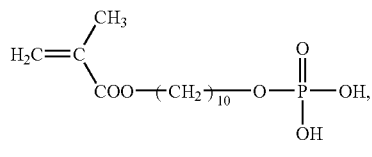

MDP 1-methacryloyloxyhexane-6-phosphate (MHP)

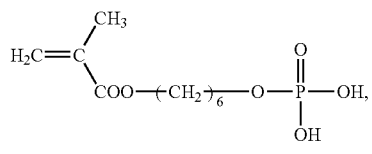

MHP 1-methacryloylaminodecane-10-phosphate (MADP)

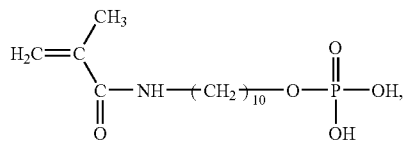

MADP 1-acryloylaminohexane-6-phosphate (AAHP)

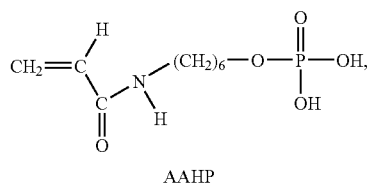

AAHP 1,3-dimethacryloyloxypropane-2-phosphate (DMPP)

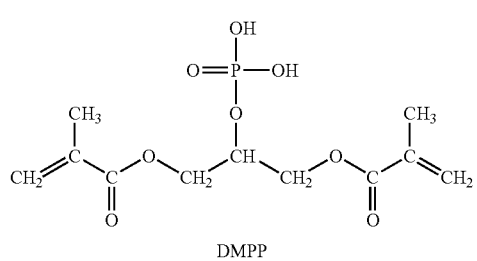

DMPP and 1,3-dimethacryloylaminopropane-2-phosphate (DMAPP)

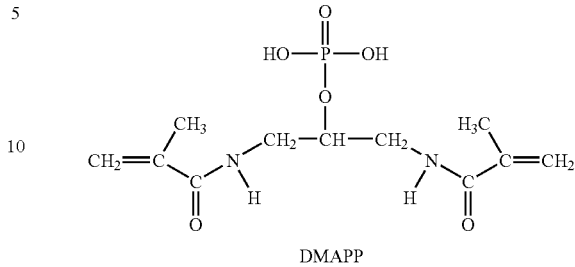

DMAPP

The most preferred phosphoric acid ester monomers are 1-methacryloyloxydecane-10-phosphate and 1-methacryloylaminodecane-10-phosphate.

Component (ii) is typically present in the adhesion-promoter composition according to the invention in a quantity of 0.05 to 25.0% by weight, preferably 0.2 to 10.0% by weight and particularly preferably 0.5 to 5.0% by weight, in each case based on the total weight of the composition.

Component (iii), the at least one sulphur-containing monomer of the general formula $R^5-R^6-S_x-R-R^5$ (IIIa) or $R^5-R^6-S_x-R^7$ (IIIb), also has at least one residue $R^5$ which contains at least one, preferably exactly one, polymerizable group. This polymerizable group is preferably radically polymerizable, thus $R^5$ typically has an ethylenically unsaturated double bond. For example $R^5$ can contain a (meth)acryloyloxy group, a (meth)acryloylamino group, a vinyl, allyl or styryl group, wherein the groups can be unsubstituted or substituted by suitable substituents. Preferred residues $R^5$ include (meth)acryloyloxy, (meth)acryloylamino, an unsubstituted or substituted vinyl group, an unsubstituted or substituted allyl group, an unsubstituted or substituted styryl group, an unsubstituted or substituted vinyl ether group, an unsubstituted or substituted vinyl ester group, an unsubstituted or substituted allyl ether group, an unsubstituted or substituted allyl ester group and vinylcyclopropyl. Possible substituents are e.g. $-COOR^8$, where $R^8$ is a straight-chained or branched $C_1$ to $C_{16}$ alkyl group, preferably $C_1$ to $C_6$ alkyl group. In one embodiment $R^5$ is an allyl ester group substituted with $-COOR^8$, preferably $-COOEt$.

$R^6$ represents an unsubstituted or substituted $C_2$ to $C_{30}$ alkylene residue, wherein the two $R^6$ residues in formula (IIIa) can be the same or different. The $C_2$ to $C_{30}$ alkylene residue is typically straight-chained or branched. $R^6$ preferably represents a $C_2$ to $C_{15}$ alkylene residue, particularly preferably a $C_2$ to $C_8$ alkylene residue.

$R^7$ in formula (IIIb) represents H or an unsubstituted or substituted $C_1$ to $C_{26}$ alkyl residue. The $C_1$ to $C_{26}$ alkyl residue is typically straight-chained or branched. $R^7$ preferably represents a $C_2$ to $C_{15}$ alkyl residue, particularly preferably a $C_2$ to $C_8$ alkyl residue.

Any substituents of the residues $R^6$ and $R^7$ present are defined as above.

Preferred sulphur-containing monomers are the disulphides, i.e. x=2 in formula (IIIa) or (IIIb).

In one embodiment of the present invention the two $R^6$ residues in formula (IIIa) or $R^6$ and $R^7$ in formula (IIIb) are joined to each other to form a heterocycle with $S_x$. The sul phur-containing monomer of component (iii) preferably then contains the following structural unit

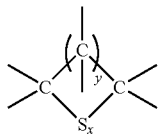

where y=1 to 8 and the C atoms are substituted with H or as previously described. Particularly preferably, x=2 and y=1, i.e. the sulphur-containing monomer contains a dithiolane ring of the following structure:

In one embodiment in formula (IIIb) $R^6=C_5$ and $R^7=C_2$, which are joined to each other to form a $C_4$-substituted dithiolane ring. In another embodiment $R^6$ is a ethylene residue in (IIIa).

Particularly suitable sulphur-containing monomers for the present invention are:
lipoic acid 2-ethoxycarbonylallyl ester (LSEAE)

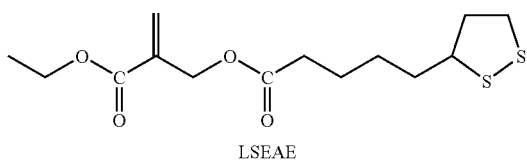

LSEAE and 2,2-bisacryloylamino diethyldisulphide (BAADS)

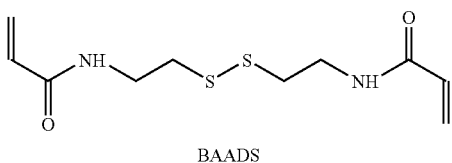

BAADS

Component (iii) is typically present in the adhesion-promoter composition according to the invention in a quantity of 0.05 to 25.0% by weight, preferably 0.2 to 10.0% by weight and particularly preferably 0.5 to 5.0% by weight, in each case based on the total weight of the composition.

The present adhesion-promoter composition can also contain mixtures of different monomers of the respective type as components (i), (ii) and (iii).

Component (iv) of the adhesion-promoter composition according to the invention is an organic solvent, typically a physiologically tolerable solvent. Suitable solvents are for example alcohols, ketones and esters and mixtures thereof, wherein methanol, ethanol, isopropanol, t-butanol, ethyl acetate, acetone, methyl ethyl ketone and mixtures thereof are preferred. Ethanol is particularly preferred. The adhesion-promoter composition typically contains 25 to 98.5% by weight, preferably 35 to 97% by weight and particularly preferably 45 to 96% by weight organic solvent (iv), in each case based on the total weight of the composition.

Furthermore, the adhesion promoter according to the invention can contain additional additives, for example to improve the mechanical properties or to set the viscosity. For example the adhesion-promoter composition can contain a filler (v), preferably an inorganic particulate filler. The fillers preferably have a particle size (determined by static light scattering or laser diffraction) in the range from 10 to 250 nm, wherein spherical particles are particularly preferred. Inorganic fillers based on oxides, in particular from pyrogenic or precipitation processes, are preferred. Suitable materials are for example, but not limited to, $ZrO_2$, $TiO_2$, $SiO_2$, $Al_2O_3$, $Ta_2O_5$ and $Yb_2O_3$ as well as mixed oxides of at least two of $SiO_2$, $ZrO_2$, $Ta_2O_5$ and $TiO_2$. Fillers which are surface-modified with polymerizable groups are particularly preferred. If present, the filler (v) is preferably contained in the adhesion-promoter composition in a maximum quantity of 10% by weight, particularly preferably 0.5 to 5.0% by weight, in each case based on the total weight of the composition.

The adhesion-promoter composition according to the present invention preferably contains a polymerization initiator (vi).

The polymerization initiator is an initiator for residue polymerization and is selected depending on whether radiation curing (photochemical radical polymerization), hot curing or curing at room temperature is desired. By "initiator" is also meant initiator systems of different compounds.

Examples of suitable photoinitiators include benzophenone, benzoin and derivatives thereof and α-diketones and derivatives thereof, such as 9,10-phenanthrenequinone, 1-phenyl-propane-1,2-dione, diacetyl and 4,4'-dichlorobenzil. Camphorquinone, 2,2-methoxy-2-phenylacetophenone or α-diketones are preferred, each in combination with amines as reducing agents, such as e.g. 4-(dimethylamino)-benzoic acid ester, N,N-dimethylaminoethyl methacrylate, N,N-dimethyl-sym-xylidine or triethanolamine, and acyl or bisacyl phosphine oxides, monobenzoyl or dibenzoyl germanium derivatives.

Benzopinacol and 2,2'-dialkylbenzopinacols for example are suitable as initiators for hot curing.

Redox-initiator combinations, such as e.g. combinations of benzoyl peroxide with N,N-dimethyl-sym-xylidine or N,N-dimethyl-p-toluidine, can be used for example as initiators for a polymerization carried out at room temperature (cold curing). In addition, redox systems consisting of peroxides and reducing agents, such as e.g. ascorbic acid, barbiturates or sulphinic acids, are also suitable.

The polymerization initiator (vi) is preferably used in a quantity of 0.001 to 3% by weight, particularly preferably 0.1 to 0.2% by weight based on the total weight of the composition.

Moreover, the adhesion-promoter composition according to the invention can contain stabilizers (vii) and polymerization inhibitors (viii), such as for example methylhydroquinone, butylhydroxytoluene (BHT) and phenothiazine.

According to a preferred embodiment, the adhesion-promoter composition according to the present invention contains:
(a) 0.05 to 25.0% by weight, preferably 0.2 to 10.0% by weight and particularly preferably 0.5 to 5.0% by weight alkoxysilane monomer(s) (i);
(b) 0.05 to 25.0% by weight, preferably 0.2 to 10.0% by weight and particularly preferably 0.5 to 5.0% by weight phosphoric acid ester monomer(s) (ii);
(c) 0.05 to 25.0% by weight, preferably 0.2 to 10.0% by weight and particularly preferably 0.5 to 5.0% by weight sulphur-containing monomer(s) (iii);

(d) 25 to 98.5% by weight, preferably 35 to 97% by weight and particularly preferably 45 to 96% by weight organic solvent (iv);
(e) 0 to 10% by weight filler (v),
(f) 0.001 to 3% by weight, preferably 0.1 to 0.2% by weight polymerization initiator (vi);
in each case based on the total weight of the composition.

Particularly preferred adhesion-promoter compositions according to the invention contain:
(A) a combination of (i) 3-methacryloyloxypropyltrimethoxysilane, (ii) 1-methacryloyloxydecane-10-phosphate and (iii) lipoic acid 2-ethoxycarbonylallyl ester;
(B) a combination of (i) 1-methacryloylaminodecane-10-phosphate, (ii) methacrylic acid (3-trimethoxysilylpropyl) amide and (iii) lipoic acid 2-ethoxycarbonylallyl ester or
(C) a combination of (i) 1-methacryloyloxydecane-10-phosphate, (ii) 3-methacryloyloxypropyltrimethoxysilane and (iii) 2,2-bisacryloylamino diethyldisulphide.

These components are preferably used in the quantities given above and optionally with the optional additives.

The adhesion-promoter composition according to the invention is used above all in dentistry and dental engineering and shows a good bonding effect between a radically curing dental material and other dental restoration materials of various types. Radically curing dental materials for use with the adhesion-promoter composition according to the invention are preferably dental filling composites or composites-based fixing materials (cements), but also adhesives and other radically curing dental materials. Dental restoration materials on which the adhesion-promoter composition according to the present invention can be used and then lead to a good bond—even after alternating thermal load—with the radically curing dental material, are for example noble metals such as gold, platinum, palladium, silver and their alloys; base metals, such as chromium, nickel, molybdenum, titanium and their alloys; siliceous ceramics, such as ceramics based on feldspar and/or quartz, leucite-containing ceramics and glass ceramics, e.g. leucite-containing glass ceramics, and non-siliceous ceramics (oxide ceramics), such as yttrium-stabilized zirconium oxide, aluminium oxide and glass-infiltrated aluminium oxide.

The adhesion-promoter compositions according to the invention are preferably used as follows to produce a bond between a radically curing dental material and another dental restoration material:

The surface of the dental restoration material is conditioned before the adhesion-promoter composition is applied, wherein the nature of the conditioning depends on the nature of the restoration material. Thus siliceous ceramics, including glass ceramic, are typically chemically etched, preferably with hydrofluoric acid, while metallic materials and non-siliceous ceramics (oxide ceramics) are typically sandblasted, for example using corundum. The pressure applied during sandblasting is preferably $10^5$ Pa (1 bar) at most.

The conditioned surface of the restoration material is then rinsed thoroughly with water, and then dried, for example by blowing with dry, oil-free air.

The adhesion-promoter composition according to the invention is applied to the thus conditioned and dried surface of the restoration material, typically in a thin layer, and preferably with a fine brush (e.g. of the Microbrush® brand), and then left to act briefly on the surface. The adhesion-promoter layer is then dried, for example by blowing with dry, oil-free air.

Finally, in the last step, the radically curing dental material is applied in order to produce the desired bond between radically curing dental material and other dental restoration material. Before the radically curing dental material is applied, the dried adhesion-promoter layer should preferably not be brought into contact with liquids, such as e.g. water, saliva or blood.

The invention is explained in more detail below by means of examples.

EXAMPLES

Example 1

Preparation of Methacrylic Acid (3-trimethoxysilylpropyl) Amide 77.4 g 3-(amino)propyltrimethoxysilane, 43.7 g triethylamine and 25 mg di-tert-butyl-p-cresol were dissolved in 500 ml dichloromethane under argon. 45.1 g methacryloyl chloride was slowly added dropwise within 1 h at −5° C., after which stirring was continued for a further 1 h at 0° C. The precipitated hydrochloride was filtered off and washed again with dichloromethane. The volatile components were removed at 40° C. under reduced pressure on the rotary evaporator. A yellow liquid with separated solid (hydrochloride) remained. The precipitation of the hydrochloride was completed by adding 150 ml diethyl ether, the precipitate was filtered off and the filtrate concentrated to small volume by introducing dry air at 40° C. on the rotary evaporator. The brownish liquid was freed from the remaining volatile components at 4 Pa ($4 \times 10^{-2}$ mbar) and the crude product (104.2 g) was distilled at a pressure of 0.06 Pa ($6 \times 10^{-4}$ mbar). The product had a boiling point of 123-125° C. 76.4 g product was obtained as a yellowish clear liquid.

Example 2

Preparation of Lipoic Acid 2-ethoxycarbonylallyl Ester LSEAE

Lipoic acid 2-ethoxycarbonylallyl ester LSEAE was prepared in two steps, as follows.

In the first step, ethyl 2-hydroxymethylacrylate was prepared by hydroxymethylation of ethyl acrylate with paraformaldehyde in the presence of diazabicyclo[2.2.2]octane (DABCO).

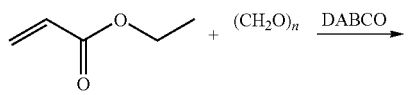

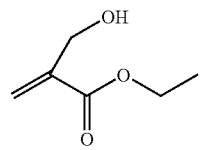

In a second step, the reaction of α-lipoic acid with ethyl 2-hydroxymethylacrylate in the presence of 4-N,N-dimethylaminopyridine and N-(3-dimethylaminopropyl)-N'-ethyl carbodiimide-hydrochloride produced lipoic acid 2-ethoxy-carbonylallyl ester (LSEAE).

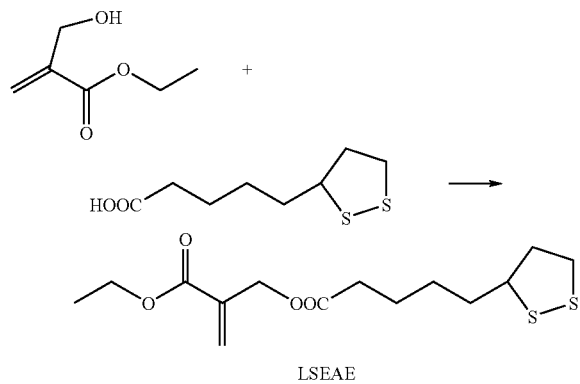

LSEAE

Step 1: Preparation of 2-hydroxymethylacrylic acid ethyl ester 2-hydroxymethylacrylic acid ethyl ester was prepared as directed by L. J. Mathias, H. Kusefoglu, Macromolec. 20 (1987) 2039-2041.

A solution of 440 g (4.4 mol) ethyl acrylate, 152 g (5.1 mol) paraformaldehyde, 48 g (0.43 mol) diazabicyclo[2.2.2]octane (DABCO) and 1 g hydroquinone monomethyl ether in 750 ml dimethyl sulphoxide was stirred for 16 h at 65° C. The addition of 880 ml water was followed by extraction with 550 ml diethyl ether. The aqueous phase was extracted 4 more times with 250 ml ether each time. The combined ether phases were then washed with 200 ml 0.5 N HCl and twice with 200 ml saturated saline solution and then dried over anhydrous sodium sulphate. After the drying agent had been removed by filtration, the solvent was drawn off on the rotary evaporator accompanied by the introduction of air and the residue was distilled under a fine vacuum. Yield: 168 g (34%) of a colourless liquid.

Step 2: Preparation of lipoic acid 2-ethoxycarbonylallyl ester (LSEAE)

2.60 g (20 mmol) 2-hydroxymethylacrylic acid ethyl ester, 4.13 g (20 mmol) α-lipoic acid, 122 mg (1.0 mmol) 4-N,N-dimethylaminopyridine and 5 mg butylhydroxytoluene (BHT) were dissolved in 40 ml methylene chloride which had been dried over a 4 Å molecular sieve. A solution of 4.54 g (22.0 mmol) N,N'-dicyclohexylcarbodiimide in 10 ml methylene chloride was then added dropwise and a white precipitate formed. The reaction mixture was then stirred for a further 6 h, before the precipitate was filtered out of the reaction mixture by means of a nutsch filter. The filter cake was washed 3 more times with 10 ml methylene chloride each time and the combined filtrate was washed 3 more times with 50 ml saturated sodium chloride solution each time. The organic phase was then dried over anhydrous sodium sulphate and the drying agent filtered off. The solvent was drawn off on the rotary evaporator accompanied by the introduction of a weak dry air stream and the residue was purified by column chromatography with n-hexane/ethyl acetate. Yield: 4.58 g (72%) of a yellow oil.

Example 3

Alkoxysilane Monomers Used (i)

3-methacryloyloxypropyltrimethoxysilane (commercially available from Fluka and Evonik Degussa GmbH), Methacrylic acid (3-trimethoxysilylpropyl) amide (example 1)

Phosphoric Acid Ester Monomers Used (ii)

1-methacryloyloxydecane-10-phosphate was prepared as described in U.S. Pat. No. 4,612,384 in a yield of 75% and a purity of 95% (determined by HPLC).

1-methacryloylaminodecane-10-phosphate was prepared as described in EP 1 674 066 in a yield of 69% and a purity of 93% (determined by HPLC).

Sulphur-Containing Monomers Used (iii)

2,2-bisacryloylamino diethyldisulphide (commercially available from Fluka)

Lipoic acid 2-ethoxycarbonylallyl ester (LSEAE; example 2)

Preparation of the Adhesion Promoters (Primers)

Adhesion-Promoter Composition A 1.0% by weight 1-methacryloyloxydecane-10-phosphate, 2.0% by weight 3-methacryloyloxypropyltrimethoxysilane and 1.0% by weight lipoic acid 2-ethoxycarbonylallyl ester dissolved in 96% by weight ethanol puriss.

Adhesion-Promoter Composition B 1.0% by weight 1-methacryloylaminodecane-10-phosphate, 2.0% by weight methacrylic acid (3-trimethoxysilylpropyl)amide and 1.0% by weight lipoic acid 2-ethoxycarbonylallyl ester dissolved in 96% by weight ethanol puriss.

Adhesion-Promoter Composition C 1.0% by weight 1-methacryloyloxydecane-10-phosphate, 2.0% by weight 3-methacryloyloxypropyltrimethoxysilane and 1.0% by weight 2,2-bisacryloylamino diethyldisulphide dissolved in 96% by weight ethanol puriss.

Adhesion-Promoter Composition D 1.0% by weight 1-methacryloyloxydecane-10-phosphate, 3.0% by weight 3-methacryloyloxypropyltrimethoxysilane, 1.0% by weight lipoic acid 2-ethoxycarbonylallyl ester dissolved in 93.5% by weight ethanol puriss. 1.5% by weight Aerosil® 200 (hydrophilic pyrogenic silicic acid with a BET surface area of approximately 200 m$^2$/g and an average primary particle size of 12 nm, available from Evonik Degussa GmbH) was added to it and the adhesion-promoter composition was homogenized in an ultrasonic flow cell.

Example 4

Determination of the Adhesion Coefficients on Different Dental Restoration Materials To determine the adhesion coefficients, a pull-off rig was used such as is described in the literature (M. Kern, V P. Thompson, J. Prost. Dent. 1995 73(3): 240-249; M. Kern, V P. Thompson, "Eine einfache Versuchsanordnung zur universellen Prüfung des Klebeverbundes im axialen Zugtest" ("A simple test rig for the general examination of the adhesive bond in the axial tensile test"), Dtsch Zahnärztl Z 1993, 48: 769-772). The results obtained are given in Table 1.

The testpieces were prepared in accordance with the protocol described in Dtsch Zahnärztl Z 1993, 48: 769-772. The cubic testpieces were surface ground with SiC abrasive paper of grit size P120-P400-P1000 accompanied by water cooling.

The individual substrate surfaces were conditioned in accordance with the corresponding manufacturer's instructions as follows. Thus siliceous surfaces were etched with hydrofluoric acid and oxidic or metallic surfaces were sandblasted with corresponding grain size and pressure.

E.max CAD was brought into contact with the hydrofluoric acid gel "Ceramic Etch" for 20 s and then carefully rinsed with distilled water.

ZirCAD, Al-Cube, Tritan, Wiron 99 and d.Sign 91 were roughened with 50 µm aluminium oxide abrasive powder (Korox 50) at 2.5×10⁵ Pa (2.5 bar) pressure from a distance of approximately 1-2 cm for 15 s.

All samples were then cleaned for 10 min. in isopropanol in an ultrasonic bath. After removal from the isopropanol, the samples were blown dry with compressed air and kept protected from dust until use.

The samples were given a single full coating of the corresponding adhesion promoter with a Microbrush® saturated with primer and the liquid was left for 60 s to take effect. Supernatant liquid was then blown off with compressed air. As described in Dtsch Zahnärztl Z 1993, 48: 769-772, a plexiglas sleeve filled with light-polymerized Multicore Flow composite (Ivoclar Vivadent A G, Schaan, Liechtenstein) was applied to the primed surface. For this, the sleeve was covered with a drop of Multilink Automix cement (Ivoclar Vivadent A G, Schaan, Liechtenstein) on the end to be bonded to and applied to the ceramic testpiece by means of press equipment. The cement was then hardened by 2×20 s exposure to a bluephase polymerization lamp and the samples were stored in water for 24 h at 37° C. The tensile adhesion was then determined with the apparatus described in the said literature and with a universal testing machine ZO10 (Zwick-Roell, Ulm, Germany).

To simulate a continuous stress, the testpieces were also subjected to an alternating thermal load. For this, the testpieces were transferred from 5° C. cold water to 55° C. hot water and back again 5000 times and in each case left in the water for 60 s.

The adhesion-promoter compositions A, B, C and D according to the invention were compared with the following commercially available ceramic and metal primers:

CP=Clearfil Ceramic Primer from Kuraray Medical Inc., Okayama, Japan (based on 3-methacryloyloxypropyl trimethoxysilane and 10-methyacryloyloxydecyl dihydrogen phosphate)

AP=Alloy Primer from Kuraray Medical Inc., Okayama, Japan (based on 6-(4-vinylbenzyl-N-propyl)amino-1,3,5-triazine-2,4-dithione and 10-methacryloyloxy-decyl dihydrogen phosphate)

MZP=MetaUZirconia Primer from Ivoclar Vivadent A G, Schaan, Liechtenstein (based on phosphonic acid methacrylate)

MS=Monobond-S primer from Ivoclar Vivadent A G, Schaan, Liechtenstein (based on 3-methacryloyloxypropyltrimethoxysilane)

TABLE 1

| Adhesion promoter composition | Initial adhesive tensile strength [MPa] | Adhesive tensile strength after alternating thermal load [MPa] |
|---|---|---|
| Substrate surface: e.max CAD (Leucite-reinforced glass ceramic from Ivoclar Vivadent AG) | | |
| A | 54.9 ± 5.5 | 55.1 ± 10.1 |
| B | 52.3 ± 8.1 | 49.8 ± 6.9 |
| C | 49.1 ± 9.4 | 47.2 ± 7.49 |
| D | 50.8 ± 7.9 | 51.9 ± 11.0 |
| Substrate surface: ZirCAD (Zirconium oxide ceramic from Ivoclar Vivadent AG) | | |
| A | 44.8 ± 7.2 | 39.8 ± 8.2 |
| D | 39.5 ± 10.4 | 40.30 ± 5.9 |
| CP* | 40.1 ± 4.5 | 35.3 ± 11.6 |
| AP* | 31.1 ± 8.9 | 26.9 ± 10.1 |
| MZP* | 27.8 ± 4.5 | 25.7 ± 8.1 |
| MS* | 9.3 ± 3.4 | — |

TABLE 1-continued

| Adhesion promoter composition | Initial adhesive tensile strength [MPa] | Adhesive tensile strength after alternating thermal load [MPa] |
|---|---|---|
| Substrate surface: Al-Cube (Aluminium oxide ceramic from VITA Zahnfabrik, Bad Säckingen) | | |
| A | 39.4 ± 11.3 | 20.9 ± 14.4 |
| B | 38.8 ± 9.9 | 22.3 ± 8.2 |
| CP* | 22.2 ± 4 | 15 ± 12.1 |
| Substrate surface: Tritan (99.5% titanium from Dentaurum, Ispringen) | | |
| A | 39.5 ± 5.6 | 21.7 ± 16.8 |
| AP* | 17.5 ± 8.5 | 11.3 ± 6.6 |
| Substrate surface: Wiron 99 (Ni/Cr/Mo alloy from BEGO, Bremen) | | |
| A | 40.3 ± 8.6 | 27.6 ± 4.9 |
| B | 34.3 ± 9.1 | 24.9 ± 10.1 |
| AP* | 28.5 ± 12.8 | 25 ± 12.2 |
| MZP* | 23.1 ± 4.8 | 14.9 ± 9.49 |
| Substrate surface: d.Sign 91 (Au/Pd/Ga alloy from Ivoclar Vivadent AG) | | |
| A | 29.7 ± 5.3 | 20.1 ± 8.2 |
| AP* | 15.7 ± 6.6 | 13.2 ± 6.8 |

*Comparison example

As the adhesion coefficients in Table 1 show, the primers A, B, C and D according to the invention are characterized by a very good bond to all the substrate surfaces tested and have a very good resistance to thermal loads. They combine the good adhesion coefficients of the commercial formulations CP, AP, MZP and MS which are, however, limited to particular surface types, with greater ease of handling. Compared with the speciality primers, A, B, C and D thus allow a substantial simplification of working procedures in day-to-day clinical work without having to accept losses in the properties obtained.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. Adhesion-promoter composition containing:
   (i) at least one alkoxysilane monomer of the general formula $$R^1{}_n Si(OR^2)_{4-n} \qquad (I),$$

in which
   $R^1$ represents a residue which has at least one polymerizable group,
   $R^2$ represents a $C_1$ to $C_8$ alkyl residue and
   n is 1, 2 or 3,
   wherein the residues $R^1$ and $R^2$ can each be the same or different;
   (ii) at least one phosphoric acid ester monomer of the general formula $$O=P(OR^3)_m(OR^4)_{3-m} \qquad (II),$$

in which
   $R^3$ represents a residue which has at least one polymerizable group,
   $R^4$ represents a residue selected from H, silyl, and $C_1$ to $C_{16}$ alkyl and
   m is 1 or 2, wherein the residues $R^3$ and $R^4$ can each be the same or different;
(iii) at least one sulphur-containing monomer which is selected from the group consisting of lipoic acid 2-ethoxycarbonylallyl ester (LSEAE) and 2,2-bisacryloylamino diethyldisulphide (BAADS); and
(iv) organic solvent.

2. A method comprising applying the adhesion-promoter composition according to claim 1 for the adhesive joining of metallic or ceramic dental materials to radically curing dental material composites and composites-based cements.

3. Adhesion-promoter composition containing:
(i) at least one alkoxysilane monomer which is selected from the group consisting of 3-methacryloyloxypropyltrimethoxysilane (MPTMS), 3-methacryloyloxypropyltriethoxysilane (MPTES), di(3-methacryloyloxypropyl)dimethoxysilane (DPDMS), and methacrylic acid (3-trimethoxysilylpropyl)amide (MTPA);
(ii) at least one phosphoric acid ester monomer of the general formula

in which
$R^3$ represents a residue which has at least one polymerizable group,
$R^4$ represents a residue selected from H, silyl, and $C_1$ to $C_{16}$ alkyl and
m is 1 or 2,
wherein the residues $R^3$ and $R^4$ can each be the same or different;
(iii) at least one sulphur-containing monomer which is selected from the group consisting of lipoic acid 2-ethoxycarbonylallyl ester (LSEAE) and 2,2-bisacryloylamino diethyldisulphide (BAADS); and
(iv) organic solvent.

4. A method comprising applying the adhesion-promoter composition according to claim 3 for the adhesive joining of metallic or ceramic dental materials to radically curing dental material composites and composites-based cements.

5. Adhesion-promoter composition containing:
(i) at least one alkoxysilane monomer which is selected from the group consisting of 3-methacryloyloxypropyltrimethoxysilane (MPTMS), 3-methacryloyloxypropyltriethoxysilane (MPTES), di(3-methacryloyloxypropyl)dimethoxysilane (DPDMS), and methacrylic acid (3-trimethoxysilylpropyl) Amide (MTPA);
(ii) at least one phosphoric acid ester monomer which is selected from the group consisting of 1-methacryloyloxydecane-10-phosphate (MDP), 1-methacryloyloxyhexane-6-phosphate (MHP), 1-methacryloylaminodecane-10-phosphate (MADP), 1-acryloylaminohexane-6-phosphate (AAHP), 1,3-dimethacryloyloxypropane-2-phosphate (DMPP) and 1,3-dimethacryloylaminopropane-2-phosphate (DMAPP);
(iii) at least one sulphur-containing monomer which is selected from the group consisting of lipoic acid 2-ethoxycarbonylallyl ester (LSEAE) and 2,2-bisacryloylamino diethyldisulphide (BAADS); and
(iv) organic solvent.

6. A method comprising applying the adhesion-promoter composition according to claim 5 for the adhesive joining of metallic or ceramic dental materials to radically curing dental material composites and composites-based cements.

* * * * *